United States Patent
Putz (10) Patent No.: US 6,415,168 B1
(45) Date of Patent: Jul. 2, 2002

(54) ELECTRICAL CONNECTOR FOR MULTI-CONTACT MEDICAL ELECTRODES

(75) Inventor: David A. Putz, Franksville, WI (US)

(73) Assignee: Ad-Tech Medical Instrument Corporation, Racine, WI (US)

( * ) Notice: Subject to any disclaimer, the term of this patent is extended or adjusted under 35 U.S.C. 154(b) by 0 days.

(21) Appl. No.: 09/552,260

(22) Filed: Apr. 19, 2000

(51) Int. Cl.[7] ................................................. A61B 5/04
(52) U.S. Cl. ....................................... 600/378; 439/909
(58) Field of Search ............................. 607/37, 38, 115, 607/116, 119, 122; 600/378, 373–381; 439/909

(56) References Cited

U.S. PATENT DOCUMENTS

| | | |
|---|---|---|
| 2,767,383 A | 10/1956 | Killian et al. |
| 3,866,615 A | 2/1975 | Hewson |
| 4,245,645 A | 1/1981 | Arseneault et al. |
| 4,341,226 A | 7/1982 | Peters |
| 4,379,462 A | 4/1983 | Borkan et al. |
| 4,461,304 A | 7/1984 | Kuperstein |
| 4,516,820 A | 5/1985 | Kuzma |
| 4,632,484 A | 12/1986 | Sinclair |
| 4,633,889 A | 1/1987 | Talalla et al. |
| 4,676,258 A | 6/1987 | Inokuchi et al. |
| 4,712,557 A | 12/1987 | Harris |
| 4,744,371 A | 5/1988 | Harris |
| 4,850,359 A | 7/1989 | Putz |
| 4,869,255 A | 9/1989 | Putz |
| 5,560,358 A | 10/1996 | Arnold et al. |
| 5,902,236 A | 5/1999 | Iversen |
| 6,025,732 A | * 2/2000 | Foo et al. ...................... 439/72 |
| 6,154,678 A | * 11/2000 | Laaro ........................... 607/115 |
| 6,162,101 A | * 12/2000 | Fischer et al. ............... 439/729 |

* cited by examiner

Primary Examiner—Linda C. M. Dvorak
Assistant Examiner—David M. Ruddy
(74) Attorney, Agent, or Firm—Jansson, Shupe & Munger, Ltd.

(57) ABSTRACT

An electrical connector for multi-contact medical electrodes with plural-contact tails, including a first elongate member having a first face and an array of electrical conductors, preferably spring-loaded ball plungers, positioned therealong and a second elongate member extending along the first elongate member and having a tail-receiving void, a second face parallel to the void with access openings to expose the plural tail contacts, the second elongate member being pivotable, between open and closed positions with respect to the first elongate member. Pivoting is about an axis along the lengths of the elongate members. The closed position serves to place the plural contacts of a tail into engagement with the electrical conductors. Some preferred embodiments include: the elongate members in nested relationship; stop surfaces defining a closed position in which the ball plungers engage the plural contacts in a just-beyond-center position; laterally-extending access openings on the second face to receive the ball plungers on pivoting; and the plural contacts being sleeves with necked-in ends to allow non-destructive withdrawal of the tail in the closed position.

20 Claims, 6 Drawing Sheets

ELECTRICAL CONNECTOR FOR MULTI-CONTACT MEDICAL ELECTRODES

FIELD OF THE INVENTION

This invention is related generally to electrical connectors for medical use and, more particularly, to medical connectors for multi-contact medical electrodes for use in facilitating surgical procedures.

BACKGROUND OF THE INVENTION

A variety of multi-contact medical electrodes, including depth electrodes, subdural strip electrodes and grid electrodes, are placed in the human body for various purposes, such as brain-mapping in epilepsy treatment. The plurality of wires necessarily extending from such electrodes typically lead to a plural-contact tail, which is a linear dielectric member with a linear array of sleeve-like contacts spaced therealong. Such plural-contact tails of multi-contact medical electrodes have been electrically joined to other equipment, such as monitoring equipment, by means of connectors designed specifically to accommodate such tails.

Many different connectors have been developed to facilitate such plural-contact connection. Examples of such prior plural-contact medical connectors are those disclosed in the following United States patents: U.S. Pat. No. 4,850,359 (Putz), U.S. Pat. No. 4,869,255 (Putz), U.S. Pat. No. 4,744,371 (Harris), U.S. Pat. No. 5,560,358 (Arnold et al.), U.S. Pat. No. 5,902,236 (Iversen), U.S. Pat. No. 4,516,820 (Kuzma), U.S. Pat. No. 4,712,557 (Harris), U.S. Pat. No. 4,461,304 (Kuperstein), U.S. Pat. No. 4,379,462 (Borkan et al.), U.S. Pat. No. 4,633,889 (Talalla et al.) and U.S. Pat. No. 4,676,258 (Inokuchi et al.).

Certain medical connectors of the prior art have a number of shortcomings and problems. Some prior connectors generally require a number of manual steps to operate, even for the final step of causing simultaneous electrical connection of the plural contacts. One-handed connection and disconnection may not be readily possible. Some prior devices require multiple parts which add to their complexity of operation.

Simplicity in structure and operation is particularly important considering that connection and disconnection typically occurs in a surgical setting, in which a surgeon or other doctor must be giving great attention to many other factors. Complexity in parts and operational procedures is a significant shortcoming, one which is important by medical personnel involved.

Maintaining reliable and constant connection throughout the period of use is another important consideration. Connectors which tend to provide electrical contact which is variable, depending on factors such as the degree of tightening, can be problematic. Still another shortcoming of certain prior art connectors is the lack of a definitive indication that electrical connection has been accomplished and put into effect.

Another concern with certain medical connectors for multi-contact electrodes, particularly in situations involving seizure disorders, is that devices essential to proper electrical connections can too easily be destroyed by inadvertent motions. More specifically, the plural-contact tails of multi-contact electrodes can break, or their plural contacts become dislodged, when forceful inadvertent yanking or pulling motions occur, as can occur during seizures. This is not a simple problem, because destruction of a plural-contact tail may make it difficult or impossible for a physician or technician to ascertain the proper association of contact leads with in-body contacts, and this makes further reliable use difficult or impossible for the in-body electrode associated with the destroyed plural-contact tail.

In summary, there remains a number of problems and shortcomings in prior connectors for use with multi-contact medical electrodes.

OBJECTS OF THE INVENTION

It is an object of this invention to provide an improved connector for multi-contact medical electrodes overcoming some of the problems and shortcomings of the prior art.

Another object of this invention is to provide an improved multi-contact medical connector which is simple in structure and operation in order to facilitate operations, including during surgery.

Another object is to provide an improved multi-contact medical connector requiring fewer manual steps to accomplish electrical connection.

Another object is to provide an improved multi-contact medical connector allowing one-handed operation in the final connection and disconnection steps.

Another object is to provide an improved multi-contact medical connector which gives highly reliable electrical connections with minimal effort.

Another object is to provide an improved multi-contact medical connector which gives a definitive indication of the completion of electrical connection.

Still another object of the invention is to provide an improved multi-contact medical connection which is less susceptible to destruction of key connection parts due to inadvertent yanking, as can occur by virtue of seizure disorders.

These and other objects of the invention will be apparent from the following descriptions and from the drawings.

SUMMARY OF THE INVENTION

This invention is an improved electrical connector for in-body multi-contact medical electrodes having linear-array plural-contact tails. The electrical connector is of the type having a tail-receiving member and means movable with respect thereto for quick connection and disconnection of all contacts.

The improved multi-contact medical connector of this invention includes first and second elongate members which are pivotable with respect to one another about a pivot axis extending along their lengths. The first elongate member has a first face and an array of electrical conductors positioned therealong in an array which matches the spacing of the plural contacts of the plural-contact tail of the medical electrode with which the connector is used. The second elongate member extends along the first elongate member and has a tail-receiving void, a second face which is parallel to the void, and access openings along the second face to expose the plural tail contacts at the second face. The second elongate member is pivotable between open and closed positions with respect to the first elongate member. The pivoting is about an axis which extends along the common lengths of the elongate members. The closed position serves to place the plural contacts of a plural-contact medical electrode tail into engagement with the electrical conductors.

In highly preferred embodiments, the second face is movable upon pivoting between the open position at which the second face is away from the first face and the closed position at which the second face is juxtaposed to the first face, and the electrical conductors are spring-loaded ball plungers along the first face which are biased toward the second face to facilitate electrical engagement with the plural contacts of the tail. The first elongate member preferably defines cylindrical wells (or "channels") along the first face which receive and hold the spring-loaded ball plungers. Such channels are preferably perpendicular to the first face. The distal ends of the ball plungers are held near the first face in positions for biased engagement against the contacts of the multi-contact tail when the first and second faces are in juxtaposition to one another.

In certain preferred embodiments, the second elongate member has proximal and distal ends and the void extends from an opening at the proximal end to a stop near the distal end, and the first elongate member includes a pair of opposed inwardly-facing endwalls between which the second elongate member extends in nested fashion with its ends adjacent to the endwalls. The proximal end of the second elongate member is that end into which the multi-contact medical electrode tail is inserted, and the distal end is the opposite end.

In certain of such preferred embodiments, one of the endwalls forms a cutaway portion through which the electrode tail passes, thereby allowing pivoting movement of the second elongate member without interference with the electrode tail. Preferably, the pivot axis extends through both endwalls and both ends and at least one pivot pin extends along a portion of the pivot axis between at least one of the endwalls and the end adjacent thereto. Two pivot pins along such axis are preferably used—one spanning between combination of endwall and end.

In preferred embodiments, the first and second elongate members have first and second stop surfaces, respectively, which abut one another to define the closed position, and at the closed position the second elongate member positions the electrode tail such that the spring-loaded ball plungers are just beyond-center (overcenter) with respect to the plural contacts of the tail. This configuration serves to provide reliable electrical contact and also helps to keep the connector in the closed position.

In certain preferred embodiments, the second elongate member includes a grip flange which serves to facilitate pivoting of the second elongate member from the closed to the open position. Such grip flange extends away from the pivot axis and provides a thumb-grip surface.

In certain highly preferred embodiments, the ball plungers protrude beyond the first face toward the second elongate member, and the access openings on the second face are designed to facilitate the closing action during which the plural contacts of the medical electrode tail are brought into engagement with the ball plungers. More specifically, the second face has a lead edge which is adjacent to the second stop surface when the second elongate member is in the closed position, and the access openings on the second face extend laterally to the lead edge such that the second elongate member has lateral openings receiving the ball plungers as the second elongate member is pivoted to the closed position.

The medical connector of this invention has significant advantages over connectors of the prior art. The connector is compact, at least in part from the fact that the orientation of the pivot axis, which is along the length of the first and second elongate members, minimizes the space in which opening and closing movement occurs. The medical connector of this invention is also very easy to use in that it can be opened and closed with one hand. The connector also provides excellent electrical connections and provides definite open and closed positions to facilitate operation and understanding.

The invention includes the medical connector as described above, and also includes the combination of such a connector with the linear-array plural-contact tails of a multi-contact medical electrode. In highly preferred embodiments, the plural contacts of the plural-contact tail are annular sleeves having necked-in (e.g., crimped) ends. This configuration of plural-contact tail with the medical connector of this invention with its spring-loaded ball plungers allows quick withdrawal of the plural-contact tail without destruction of the plural-contact tail. A sudden pull allows the plural-contact tail to pull out from the connector even while the connector is in its closed position. This is brought about by the combination of spring-loaded ball plungers and the necked-in annular-sleeve contacts. The contacts will ride right over the line of ball plungers without causing destruction of the plural-contact tail.

This advantage is significant in that it minimizes or prevents the problems which can occur if a patient's seizure causes violent jerking and yanking movements during e.g., a brain-mapping session. Such activity can result in the need for an expensive and time-consuming reorganization and reassembly of electrical components in order to allow resumption of the intended medical activity.

BRIEF DESCRIPTION OF THE DRAWINGS

The drawings illustrate a preferred embodiment including the above-noted characteristics and features of the invention. The invention will be readily understood from the descriptions and drawings. In the drawings.

DETAILED DESCRIPTION OF PREFERRED EMBODIMENTS

FIGS. 1–6 illustrate an improved electrical connector 10 for use with an in-body multi-contact medical electrode (the in-body portion of which is not shown) having a linear-array plural-contact tail 12, having a linear array of electrical contacts 14 spaced therealong, each electrically linked by a tiny conductive wire running up and beyond tail 12 to a particular in-body contact on the in-body portion of the electrode. Connector 10 includes first and second elongate members 16 and 18 which are pivotable with respect to one another about a pivot axis A which extends along their lengths.

First elongate member 16 has a first face and an array of spring-loaded ball plungers 22 positioned therealong in a linear array which matches in its spacing the linear array of electrical contacts 14 of plural-contact tail 12. Second elongate member 18 extends along first elongate member 16 and has a linear tail-receiving void 24, a second face 26 which is parallel with and closely adjacent to void 24, and access openings 28 along second face 26 and intersecting void 24 to expose contacts 14 at second face 26 in positions of alignment with, and intersecting, the round distal ends 22a of spring-loaded ball plungers 22.

Figure 1:
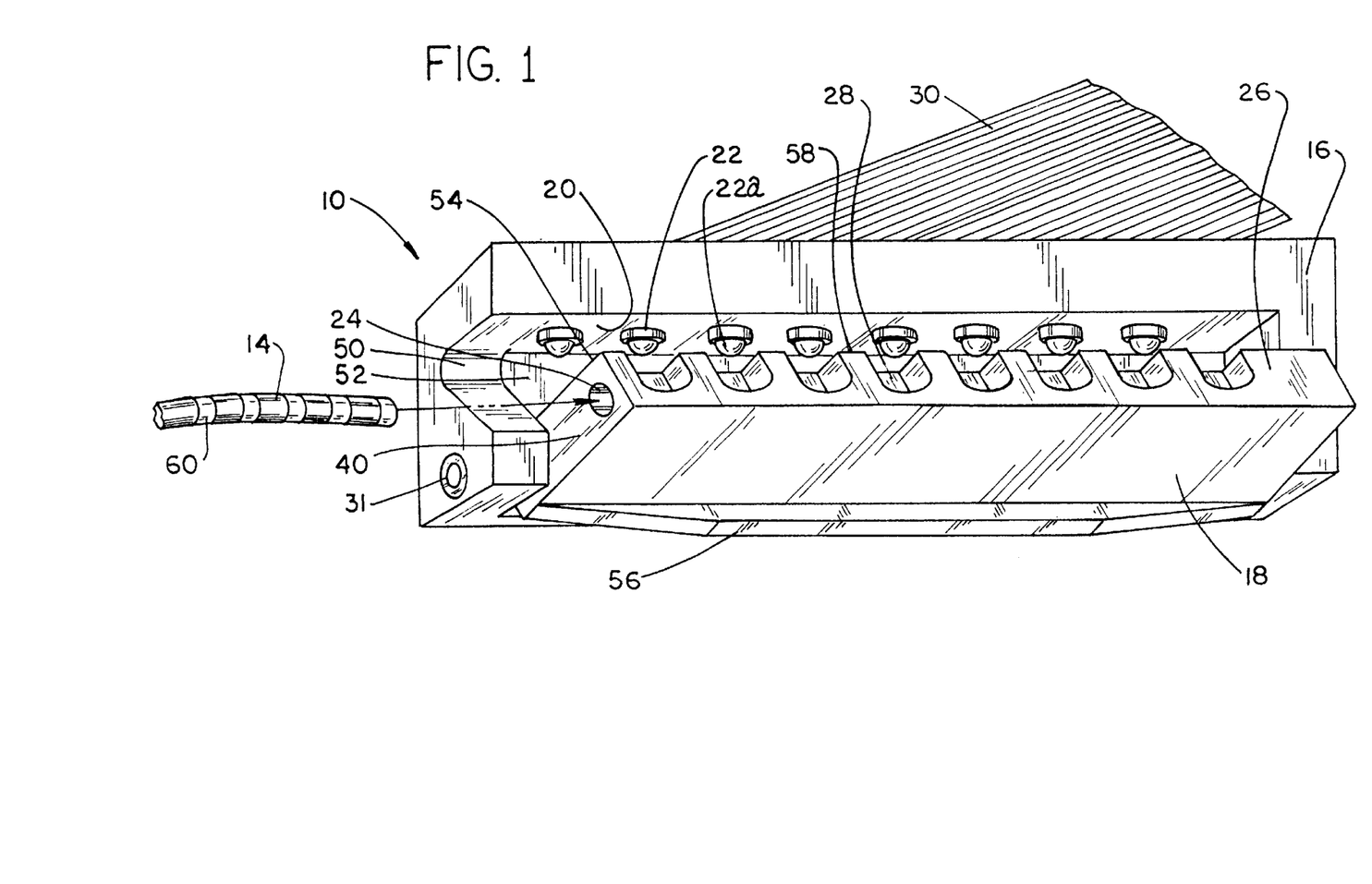
FIG. 1 is a perspective view of the connector in an open condition, with the plural-contact tail of an in-body medical electrode in position for insertion into the connector.
Figure 2:
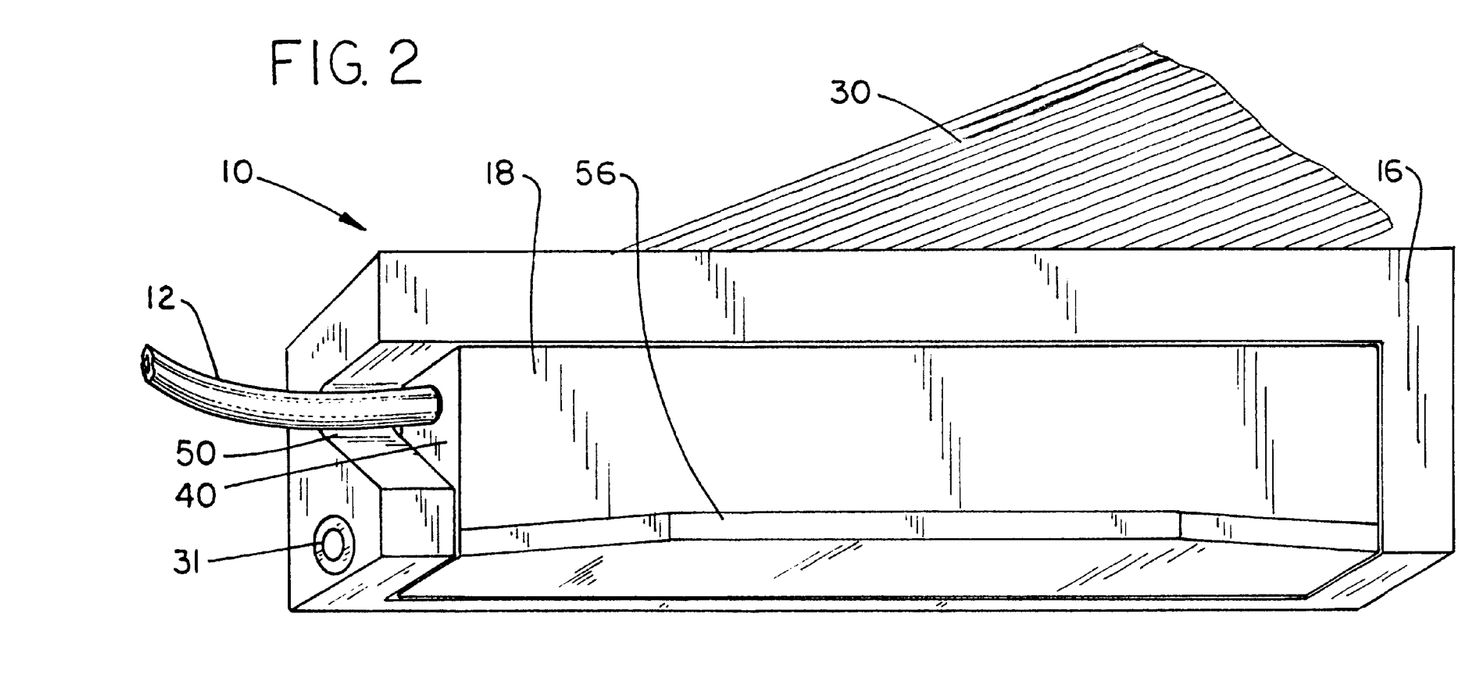
FIG. 2 is a perspective view as in FIG. 1, but with the connector in closed condition.
Figure 3:
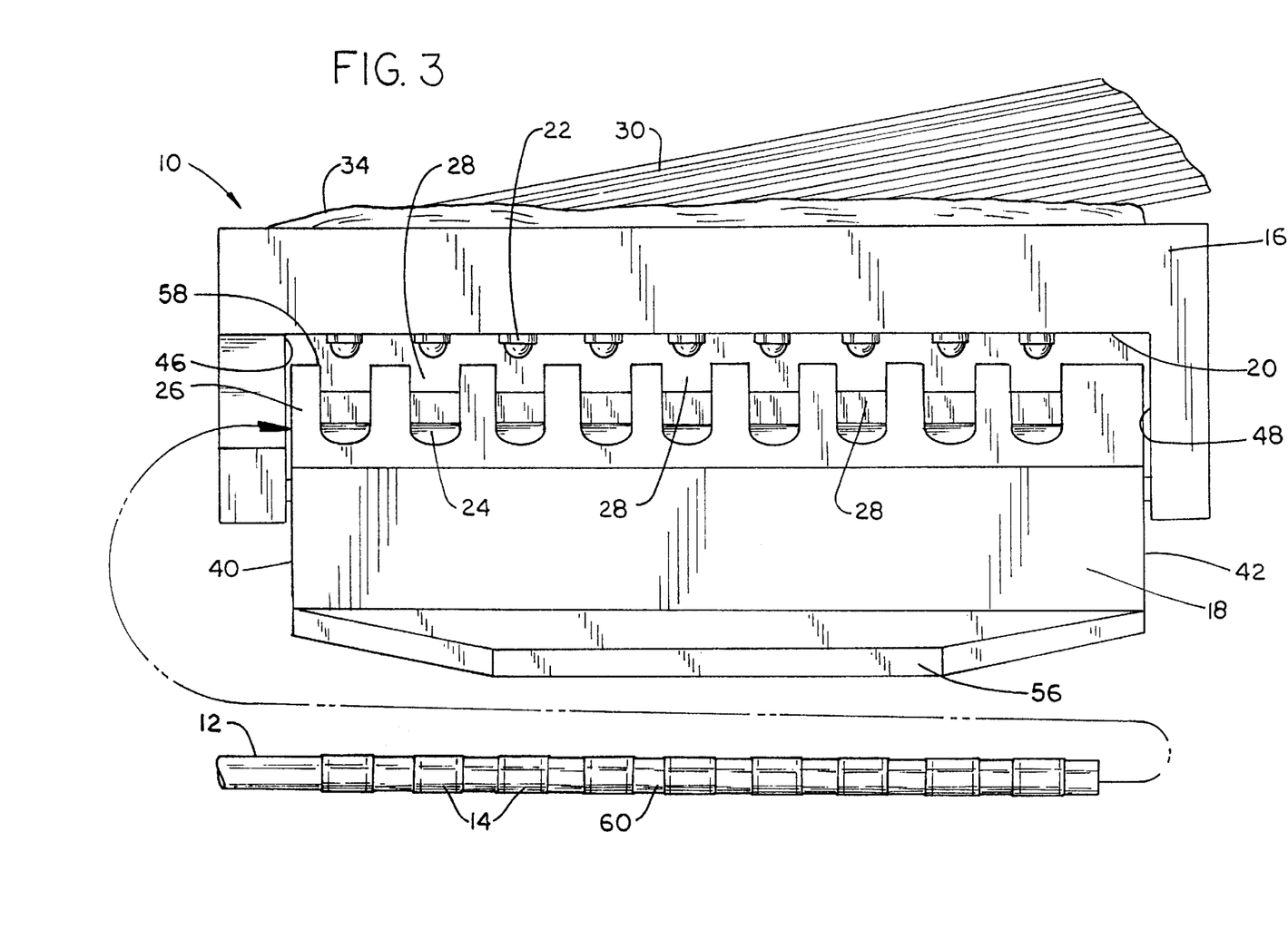
FIG. 3 is a front elevation of FIG. 1.
Figure 4:
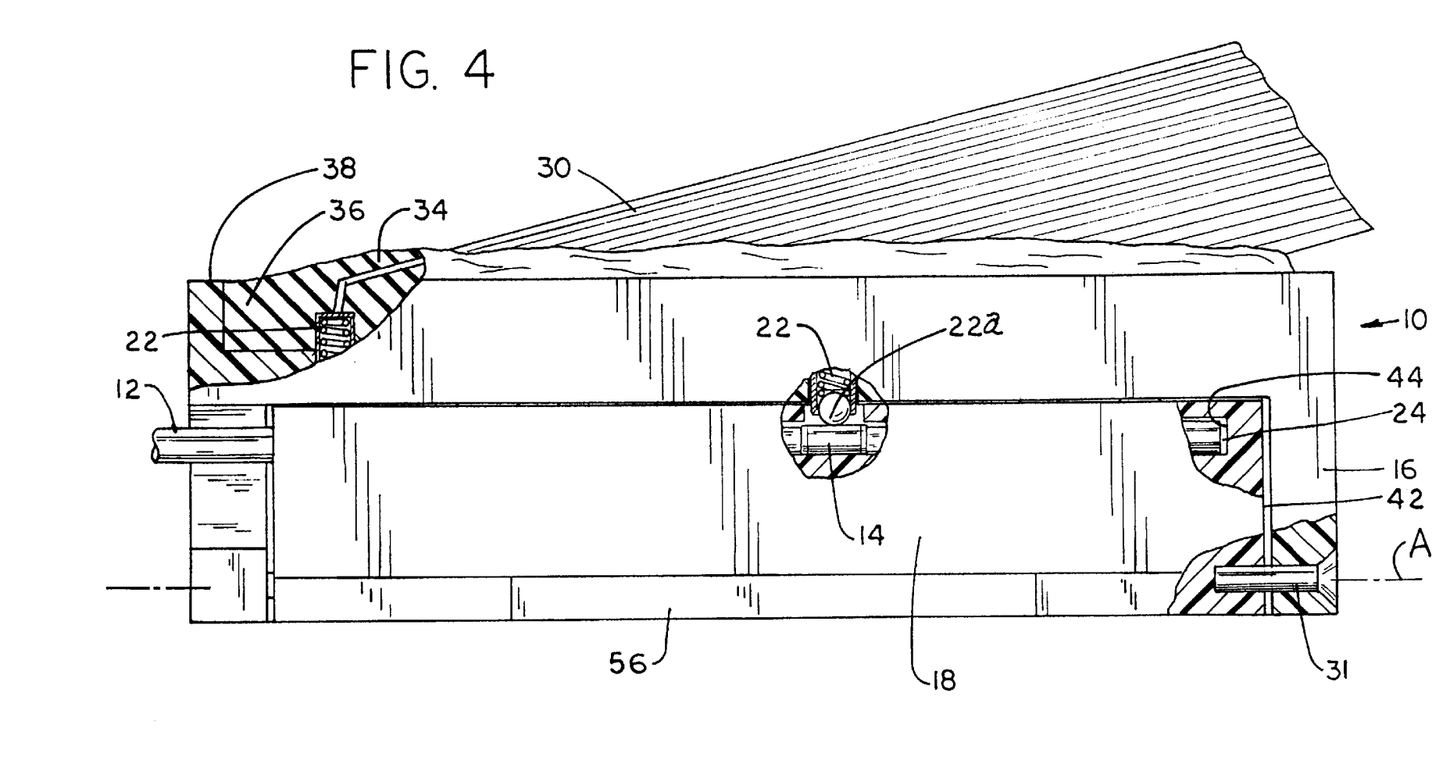
FIG. 4 is a front elevation of FIG. 2, but with cutaway portions to illustrate certain internal details.
Figure 5:
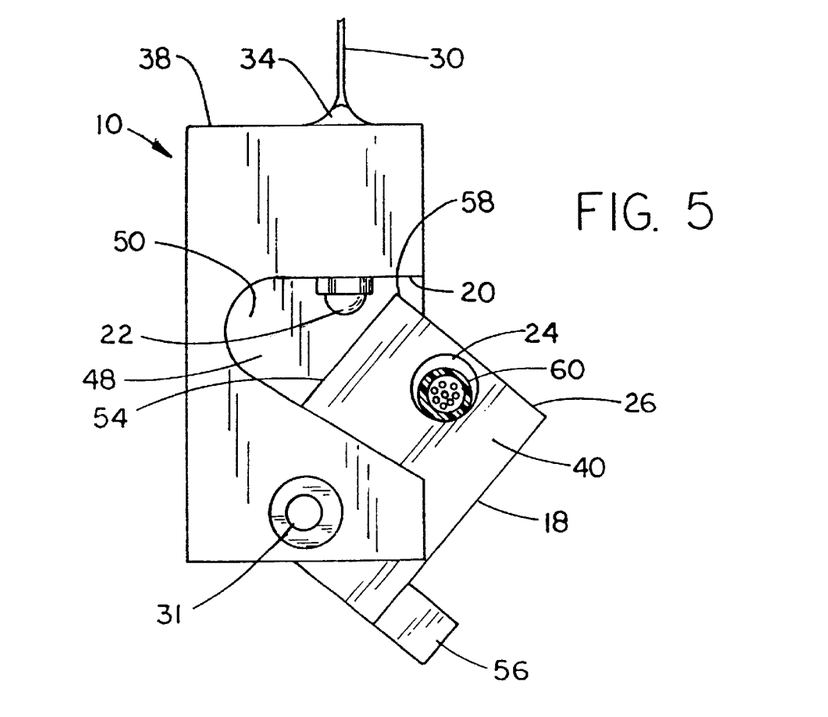
FIG. 5 is a left side elevation of the connector, with the tail in section, showing the connector just before it is closed.
Figure 6:
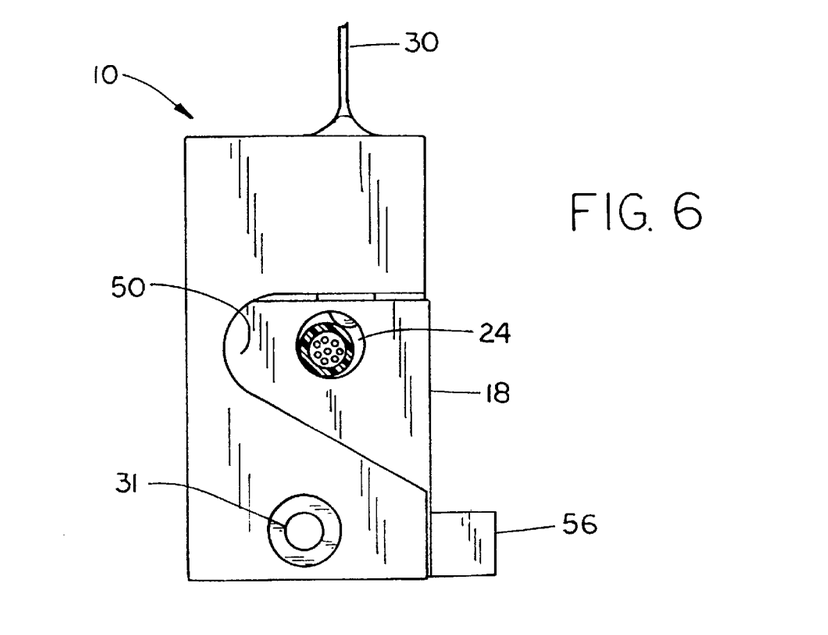
FIG. 6 is a left side elevation as in FIG. 5, but with the connector fully closed.

Second elongate member 18 pivots with respect to first elongate member 16 between open positions illustrated by FIGS. 1, 3 and 5 and a closed position illustrated by FIGS. 2, 4 and 6. Pivot pins 31 (see cutaway portion of FIG. 4) extend along axis A and pivotably connect second elongate member 18 with first elongate member 16. In the closed position, second face 26 is closely adjacent (juxtaposed) to first face 18, such that contacts 14 are placed into engagement with spring-loaded ball plungers 22, each of which is electrically connected to one of the wires 30 which extend from connector 10 for easy connection by means not shown with other equipment.

First elongate member 16 preferably defines wells (or "channels") 32 along first face 20 which receive and hold spring-loaded ball plungers 22. Channels 32 are perpendicular to first face 20 and extend through first elongate member 16 to allow electrical connection with wires 30. Spring-loaded ball plungers 22 are potted in their positions in channels 32 and protruding just beyond first face 20 by an epoxy 34 applied in a recess 36 (see cutaway portion of FIG. 4) which is formed in the outer surface 38 of first elongate member 16. Distal ends 22a of spring-loaded ball plungers 22 are biased toward second face 26 to facilitate electrical engagement with contacts 14 of tail 12.

Second elongate member 18 has proximal and distal ends 40 and 42, and linear void 24 extends from an opening at proximal end 40 to a stop 44 near distal end 42. The position of stop 44 is fixed such that full insertion of tail 12 into void 24 causes contacts 14 to be in alignment with access openings 28 along second face 26 of second elongate member 18. First elongate member 16 includes a pair of opposed inwardly-facing endwalls 46 and 48 between which second elongate member 18 extends in nested fashion, with ends 40 and 42 adjacent to endwalls 46 and 48, respectively. As shown best in FIGS. 5 and 6, endwall 46, which is adjacent to proximal end 40 of second elongate member 18, is formed with a cutaway portion 50 to accommodate the presence of electrode tail 12 during pivoting movement of second elongate member 18.

As shown best in FIGS. 5 and 6, first and second elongate members 16 and 18 have first and second stop surfaces 52 and 54, respectively, which abut one another to define the closed position. As seen best in FIG. 6, at the closed position second elongate member 18 positions tail 12 such that spring-loaded ball plungers 22 are just beyond-center with respect to contacts 14 of tail 12.

Second elongate member 18 includes an integrally-formed grip flange 56 (see FIGS. 5 and 6), which extends away from pivot axis A. To open connector 10, downward thumb pressure is applied on grip flange 56 to pivot second elongate member 18 away from the closed position shown in FIG. 6.

As shown best in FIG. 3, second face 26 has a lead edge 58 which is adjacent to second stop surface 54 (and to first stop surface 52) when second elongate member 18 is in the closed position. Access openings 28 on second face 26 extend laterally on second face 26 to lead edge 58. This provides a lateral opening to each access openings 28 to receive spring-loaded ball plungers 22 as second elongate member 18 is pivoted to the closed position.

Figure 7:
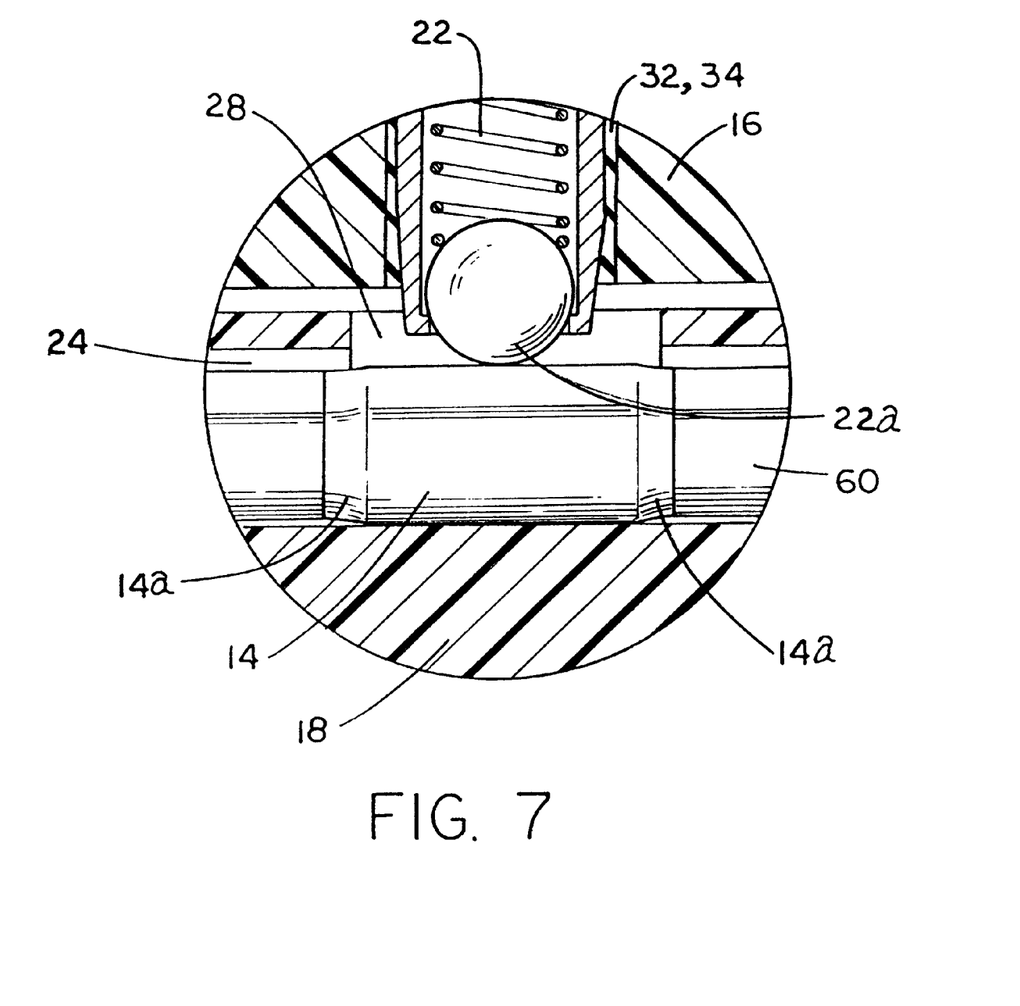
FIG. 7 is an enlarged fragmentary cutaway view of a portion of FIG. 4, as indicated in FIG. 4.

FIG. 7 illustrates details of contacts 12 and their relationship to distal ends 22a of spring-loaded ball plungers 22. Each contact 14 of plural-contact tail 12 is an annular sleeve which includes necked-in ends 14a, formed by crimping. As can be seen, the outer diameter of contact sleeves 14 are slightly greater than the outer diameter of the adjacent dielectric support tube 60 along which contacts 14 are mounted. As earlier noted, this allows quick removal of plural-contact tail 12 from medical connector 10, inadvertent or otherwise, without causing destruction of plural-contact tail 12.

First and second elongate members 16 and 18 of medical connector 10 may be made of hard plastic materials, a wide choice of which is available and will be apparent to those receiving this disclosure. Second elongate member 18 is preferably made of translucent or transparent material so that the positions of contacts 14 can be seen even without looking at access openings 28. A wide variety of materials is available for the various parts discussed and illustrated herein.

While the principles of this invention have been described in connection with specific embodiments, it should be understood clearly that these descriptions are made only by way of example and are not intended to limit the scope of the invention.

What is claimed is:

1. In an electrical connector for in-body multi-contact medical electrodes with linear-array plural-contact tails, having a tail-receiving member and means movable with respect thereto for quick connection and disconnection of all contacts, the improvement comprising:
  a first elongate member having a first face and an array of electrical conductors positioned therealong; and
  a second elongate member extending along the first elongate member and having a tail-receiving void, a second face parallel to the void with access openings to expose the plural tail contacts, the second elongate member being pivotable, between open and closed positions with respect to the first elongate member, about an axis extending along the lengths of the elongate members, the closed position serving to place the plural contacts of a tail into engagement with the electrical conductors.

2. The multi-contact medical connector of claim 1 wherein:
  the second face is movable upon pivoting between the open position at which the second face is away from the first face and the closed position at which the second face is juxtaposed to the first face; and
  the electrical conductors are spring-loaded ball plungers along the first face and biased toward the second face to facilitate electrical engagement with the plural contacts of the tail.

3. The multi-contact medical connector of claim 2 wherein the first elongate member defines wells along the first face holding the spring-loaded ball plungers.

4. The multi-contact medical connector of claim 2 wherein:
  the second elongate member has proximal and distal ends and the void extends from an opening at the proximal end to a stop near the distal end; and
  the first elongate member includes a pair of opposed inwardly-facing endwalls between which the second elongate member extends in nested fashion with its ends adjacent to the endwalls.

5. The multi-contact medical connector of claim 4 wherein the pivot axis extends through both endwalls and both ends and at least one pivot pin extends along a portion of the pivot axis between at least one of the endwalls and the end adjacent thereto.

6. The multi-contact medical connector of claim 4 wherein one of the endwalls forms a cutaway portion through which the electrode tail passes, thereby allowing pivoting movement of the second elongate member without interference with the electrode tail.

7. The multi-contact medical connector of claim 2 wherein:

the first and second elongate members have first and second stop surfaces, respectively, which abut one another to define the closed position; and at the closed position the second elongate member positions the electrode tail such that the spring-loaded ball plungers are just beyond-center with respect to the plural contacts of the tail, thereby providing reliable electrical contact and helping to maintain the closed position.

8. The multi-contact medical connector of claim 7 wherein the second elongate member includes a grip flange facilitating pivoting the second elongate member from the closed to the open position.

9. The multi-contact medical connector of claim 7 wherein the first elongate member defines wells along the first face holding the spring-loaded ball plungers.

10. The multi-contact medical connector of claim 9 wherein: the ball plungers protrude beyond the first face toward the second elongate member;

the second face has a lead edge which is adjacent to the second stop surface when the second elongate member is in the closed position; and the access openings on the second face extend laterally to the lead edge such that the second elongate member has lateral openings receiving the ball plungers as the second elongate member is pivoted to the closed position.

11. In combination, (a) an electrical connector for in-body multi-contact medical electrodes with linear-array plural-contact tails, having a tail-receiving member and means movable with respect thereto for quick connection and disconnection of all contacts and (b) a linear-array plural-contact tail, the improvement comprising:

a first elongate member having a first face and an array of electrical conductors positioned therealong; and a second elongate member extending along the first elongate member and having an elongate void with the plural-contact tail received therein, a second face parallel to the void with access openings exposing the plural tail contacts, the second elongate member being pivotable, between open and closed positions with respect to the first elongate member, about an axis extending along the lengths of the elongate members, the plural contacts engaged with the electrical conductors in the closed position.

12. The combined medical connector and multi-contact tail of claim 11 wherein:

the second face is movable upon pivoting between the open position at which the second face is away from the first face and the closed position at which the second face is juxtaposed to the first face; and the electrical conductors are spring-loaded ball plungers along the first face and biased toward the second face to facilitate electrical engagement with the plural contacts of the tail.

13. The combined medical connector and multi-contact tail of claim 12 wherein the plural contacts of the tail are annular sleeves having necked-in ends, thereby allowing quick withdrawal of the plural-contact tail without destruction thereof.

14. The combined medical connector and multi-contact tail of claim 12 wherein the first elongate member defines wells along the first face holding the spring-loaded ball plungers.

15. The combined medical connector and multi-contact tail of claim 12 wherein:

the second elongate member has proximal and distal ends and the void extends from an opening at the proximal end to a stop near the distal end; and the first elongate member includes a pair of opposed inwardly-facing endwalls between which the second elongate member extends in nested fashion with its ends adjacent to the endwalls.

16. The combined medical connector and multi-contact tail of claim 15 wherein the pivot axis extends through both endwalls and both ends and at least one pivot pin extends along a portion of the pivot axis between at least one of the endwalls and the end adjacent thereto.

17. The combined medical connector and multi-contact tail of claim 15 wherein one of the endwalls forms a cutaway portion through which the electrode tail passes, thereby allowing pivoting movement of the second elongate member without interference with the electrode tail.

18. The combined medical connector and multi-contact tail of claim 12 wherein:

the first and second elongate members have first and second stop surfaces, respectively, which abut one another to define the closed position; and at the closed position the second elongate member positions the electrode tail such that the spring-loaded ball plungers are just beyond-center with respect to the plural contacts of the tail, thereby providing reliable electrical contact and helping to maintain the closed position.

19. The combined medical connector and multi-contact tail of claim 17 wherein the first elongate member defines wells along the first face holding the spring-loaded ball plungers.

20. The combined medical connector and multi-contact tail of claim 19 wherein:

the ball plungers protrude beyond the first face toward the second elongate member;

the second face has a lead edge which is adjacent to the second stop surface when the second elongate member is in the closed position; and the access openings on the second face extend laterally to the lead edge such that the second elongate member has lateral openings receiving the ball plungers as the second elongate member is pivoted to the closed position.

* * * * *